United States Patent
Mena Benito et al.

(10) Patent No.: US 11,744,559 B2
(45) Date of Patent: Sep. 5, 2023

(54) SYSTEM AND METHOD FOR UNOBTRUSIVELY DETERMINING A FERTILE WINDOW

(71) Applicant: KONINKLIJKE PHILIPS N.V., Eindhoven (NL)

(72) Inventors: Maria Estrella Mena Benito, Eindhoven (NL); Laurentia Johanna Huijbregts, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 873 days.

(21) Appl. No.: 16/486,508

(22) PCT Filed: Feb. 12, 2018

(86) PCT No.: PCT/EP2018/053420
§ 371 (c)(1),
(2) Date: Aug. 16, 2019

(87) PCT Pub. No.: WO2018/149784
PCT Pub. Date: Aug. 23, 2018

(65) Prior Publication Data
US 2020/0229800 A1    Jul. 23, 2020

(30) Foreign Application Priority Data
Feb. 16, 2017    (EP) .................... 17156536

(51) Int. Cl.
*A61B 10/00*    (2006.01)
*A61B 5/08*    (2006.01)
(Continued)

(52) U.S. Cl.
CPC ........ *A61B 10/0012* (2013.01); *A61B 5/0816* (2013.01); *A61B 5/1135* (2013.01);
(Continued)

(58) Field of Classification Search
CPC ... A61B 10/0012; A61B 5/0816; A61B 5/681; A61B 5/6804; A61B 5/1135; A61B 5/14552; A61B 5/4318
See application file for complete search history.

(56) References Cited

U.S. PATENT DOCUMENTS 7,704,211 B1 * 4/2010 Koh .................. A61B 5/14551
                                                        600/300
9,316,594 B2   4/2016 Kane
(Continued)

FOREIGN PATENT DOCUMENTS

WO    WO2012143721 A1    10/2012
WO    WO2015143259 A1    9/2015
(Continued)

OTHER PUBLICATIONS

PCT International Search Report, International application No. PCT/EP2018/053420, dated Apr. 26, 2018.
(Continued)

*Primary Examiner* — Benyam Haile (57) ABSTRACT

A system for unobtrusively determining a fertile window includes a contact sensor in contact with the woman and configured to provide a signal indicative of respiration of the woman. A processor is configured to process the signal to obtain a biomechanical parameter indicative of the respiration, and determine the fertile window of the woman based on a change in the obtained biomechanical parameter.

16 Claims, 3 Drawing Sheets

(51) Int. Cl.
    *A61B 5/113* (2006.01)
    *A61B 5/1455* (2006.01)
    *A61B 5/00* (2006.01)
(52) U.S. Cl.
    CPC ........ *A61B 5/14552* (2013.01); *A61B 5/4318* (2013.01); *A61B 5/681* (2013.01); *A61B 5/6804* (2013.01)

(56) References Cited

U.S. PATENT DOCUMENTS

| | | |
|---|---|---|
| 2008/0146892 A1 | 6/2008 | Leboeuf |
| 2013/0178717 A1 | 7/2013 | Krammer |
| 2013/0231582 A1 | 9/2013 | Prasad |
| 2013/0296735 A1 | 11/2013 | James |
| 2016/0058428 A1 | 3/2016 | Shinar |
| 2016/0058429 A1* | 3/2016 | Shinar ............ A61B 10/0012 600/551 |
| 2016/0066894 A1* | 3/2016 | Barton-Sweeney ................. A61B 10/0012 600/301 |
| 2016/0174898 A1 | 6/2016 | Udoh |
| 2016/0213354 A1 | 7/2016 | Levin |
| 2016/0374608 A1* | 12/2016 | Dugan ................ A61B 5/746 600/301 |
| 2017/0112671 A1* | 4/2017 | Goldstein ........... H04R 25/554 |
| 2017/0360329 A1* | 12/2017 | Derkx .............. A61B 5/7203 |
| 2019/0167236 A1* | 6/2019 | Maas ................ A61B 5/103 |

FOREIGN PATENT DOCUMENTS

| | | |
|---|---|---|
| WO | WO2015150434 A1 | 10/2015 |
| WO | WO2016063082 A1 | 4/2016 |
| WO | WO2016083807 A1 | 6/2016 |
| WO | WO2016131630 A1 | 8/2016 |

OTHER PUBLICATIONS

Observations on the PCT International Search Report and the Written Opinion of International Application No. PCT/EP2018/053420, dated Jul. 6, 2018.

England S. J. et al., "Fluctuations in Alveolar C02 and in Base Excess During the Menstrual Cycle", Respiration Physiology, Amsterdam, NL, vol. 26, No. 2, pp. 157-161, Apr. 1, 1976 (Apr. 1, 1976), pp. 157-161, XP02SI97646.

Stanford, J. B. et al., "Timing Intercourse to Achieve Pregnancy: Current Evidence", Obstetrics & Gynecology100.6 (2002): 1333-1341.

Bigelow, J.L. et al. , "Mucus Observations in the Fertile Window: A Better Predictor of Conception than Timing of Intercourse", European Society of Human Reproduction and Embryology, vol. 19, No. 4, Feb. 2004, pp. 889-892.

Wilcox, A.J. et al., "The Timing of the "Fertile Window" in the Menstrual Cycle: Day Specific Estimates from a Prospective Study", BMJ, vol. 321, Nov. 18, 2000, pp. 1259-1262.

Hadžiomerovic, D. et al., "The Biphasic Pattern of End-Expiratory Carbon Dioxide Pressure: A Method for Identification of the Fertile Phase of the Menstrual Cycle", 2008 American Society for Reproductive Medicine, Fertility and Sterility, vol. 90, issue 3, Sep. 2008, pp. 731-736.

Chandra, S. et al., "Effect of End Tidal Carbon Dioxide Concentration on Different Phases of Menstrual Cycle in Subjects Suffering with Premenstrual Syndrome", IOSR Journal of Dental and Medical Sciences (JDMS), vol. 1, Issue 4, Sep.-Oct. 2012, pp. 29-33.

Eberhard et al., "The Design, Use, and Results of Transcutaneous Carbon Dioxide Analysis: Current and Future Directions", International Anesthesia Research Society, Anesth Analg., vol. 105, No. 6, Dec. 2007, pp. S48-52.

Tshu, C. et al., "Tempdrop Is A Wearable Body Temperature Sensor For Fertility Tracking", Downloaded from the Internet Aug. 14, 2019, https://techcrunch.com/2014/04/11/tempdrop-is-a-wearable-body-temperature-sensor-for-fertility-tracking/.

"Determining Your Fertility Window, Getting Pregnant", American Pregnancy Association Downloaded from the Internet Aug. 14, 2019, http://americanpregnancy.org/getting-pregnant/fertility-window/.

Peck, E., "From Ovulation to Pregnancy: The Best Fertility Trackers and Wearables", Health and Wellbeing Feature, pp. 1-14, Apr. 25, 2018, http://www.wareable.com/health-and-wellbeing/fertility-tracking-tech-wearables-and-apps-to-help-couples-conceive.

"Myotrace: An Evaluation of a Novel Critical Illness Monitoring System", US National Library of Medicine, May 26, 2011, https://clinicaltrials.gov/ct2/show/NCT01361451.

\* cited by examiner

SYSTEM AND METHOD FOR UNOBTRUSIVELY DETERMINING A FERTILE WINDOW

CROSS REFERENCE TO RELATED APPLICATIONS

This patent application claims the priority benefit under 35 U.S.C. § 371 of International Patent Application no. PCT/EP2018/053420, filed Feb. 12, 2018, which claims the benefit of European Patent Application No. EP17156536.9, filed on Feb. 16, 2017. These applications are hereby incorporated by reference herein in their entirety.

FIELD OF THE INVENTION

The invention relates to a system, method and corresponding computer program for unobtrusively determining a fertile window. In particular, it relates to a wearable system such as integrated in a bra for supporting personalized prediction of the fertile window for a planned parent-hood purpose. However, the invention is not limited to this field and in other applications the system can be used for predicting menstruation and helping in menstruation related symptoms, for instance.

BACKGROUND OF THE INVENTION

Subfertility is experienced by a large proportion of the world's population, with involuntary childlessness experienced at some stage by between 12% and 28% of couples. Subfertility rates have increased by 4% since the 1980s, in part due to an increase in the age of having children. Conception can only take place during the fertile window, which generally runs from the five days before ovulation through to the day of ovulation. Therefore, couples trying to conceive should have intercourse in the fertile window. However, determining the fertile window is not straightforward.

The key of maximizing the chances of getting pregnant each menstrual cycle is to be able to accurately identify a woman's personal fertile days. Many women count days from the starting day of their menstrual bleeding or use a fertility tracking app, such as Glow or Ovuline, to find out which day their ovulation is or to estimate whether a given day is favorable for getting pregnant. Since the fertile window is highly individual and can vary per month, the result is highly inaccurate. Despite the fact that the mechanism of menstruation is repetitive, it appears irregular most times.

Disposable and reusable modules exist for measuring temperature, hormone and electrolyte levels which can all be indicative of ovulation and/or the fertile window. These products use information obtained from oral and vaginal sensors. For example ovulation kits, detect the presence of luteinizing hormone (LH) in women's urine. Ovulation microscopes or saliva scopes allow women to identity their most fertile days by observing visual changes that take in saliva throughout the monthly cycle. Basal body thermometers help women track their ovulation cycle by reading their basal body temperature, for example by means of wearable body temperature sensors (Clear Blue, Ovacue). Another example is the OV Watch from HealthWatchSystems. The OV watch is designed to detect the surge of chloride-ions associated with an increase of reproductive hormones in woman's system before she ovulates.

Unfortunately, the described methods and devices require discipline, or are obtrusive, inaccurate or embarrassing. For example, the use of basal thermometers is not so simple and taking accurate readings can be difficult, because temperatures need to be recorded around the same time each morning and can be thrown off by factors like poor sleep. Detection of hormone levels implicates to pee on an ovulation stick and interpretation of results is not always reliable. The chloride-ion level measured with the OV Watch depends on several confounding factors, like sweating, dehydration and salt consumption, which could result in false detection or non-detection of the fertile window. Next to that, a watch is visible to everyone, while the woman might want to hide that she is trying to conceive and/or that she is experiencing problems with conceiving due to subfertility of either herself or her partner.

WO 2015/150434 A1 relates to a system for unobtrusive fertility tracking, comprising a sensor for obtaining a heart signal, a processing unit configured to determine a subject's heart rate from the heart signal, and an evaluation unit configured to analyze the subject's heart rate to predict likelihood of ovulation. The processing unit is further configured to extract heart rate variability features from the heart signal, and the evaluation unit is further configured to predict likelihood of ovulation based on the heart rate variability features.

WO 2015/143259 A1 relates to a system and method for determining a user's physical condition such as a hormonal level. The system includes a portable or wearable device that measures multiple biomarkers, such as basal body temperature, saliva salinity, saliva pH, sweat ions, skin thickness, vitamin levels, mineral levels, or breath carbon dioxide. The system determines the physical condition, such as the fertility level of the user based on comparing the measured biomarkers with data models.

However, in some applications heart rate, heart rate variability and/or biomarkers will not allow to accurately predict ovulation or are difficult to obtain. The need thus exists for alternative unobtrusive systems and methods that do not solely rely on heart rate, heart rate variability or biomarkers.

SUMMARY OF THE INVENTION

It is therefore an object of the present invention to provide a system, a corresponding method and a corresponding computer program which allow a reliable and unobtrusive determination of a fertile window of a woman.

According to an aspect of the present invention, a system for determining a fertile window of a woman is provided. The system comprises a contact sensor unit for providing a signal in contact with the woman, wherein the signal is indicative of respiration of the woman, and a processing unit for processing the signal to obtain a biomechanical parameter indicative of respiration. The processing unit is configured to determine the fertile window of the woman based on a change in the obtained biomechanical parameter.

Since the fertile window of the woman is determined based on a change in the obtained parameter, which is indicative of respiration and determined from a signal of a contact sensor unit, the fertile window can be determined without relying on, for instance, the heart rate of the woman. It is known that respiration changes with the menstrual cycle, using the biomechanical parameter indicative of respiration for determining the fertile window thus allows for an accurate determination of the fertile window. Accordingly, by processing the signal indicative of respiration and by recognizing changes in the obtained parameters, the change in respiration with the menstrual cycle can be determined. Further, since the change in respiration occurs at several days before ovulation, it is advantageously possible to associate a determined change with an onset of the fertile window.

The biomechanical parameter includes at least one of minute volume, tidal volume, respiratory drive, respiration rate and thorax expansion. A biomechanical parameter in general is a parameter, which can be obtained from the signal of the contact sensor, and which is capable of describing at least one of structure and function of the woman by methods of mechanics. The biomechanical parameter allows to be determined more accurately and with less influence to environmental conditions as compared to, for instance, a biochemical sensor, a thermal sensor or a biomarker.

Previously known systems, for instance, rely on the basal body temperature and identify an increase of the basal body temperature with the onset of the fertile window. However, basal body temperature only increases shortly before ovulation, while the change in obtained parameter indicative of respiration allows the determination of the entire fertile window, i.e. respiration changes earlier and correlates better with the fertile window than an increase in basal body temperature can be detected.

In an embodiment the fertile window comprises the day of ovulation and the five days before ovulation. During the average woman's menstrual cycle there are six days when intercourse can result in pregnancy; this "fertile window" comprises preferably the five days before ovulation and the day of ovulation itself, as described, for instance, by Stanford, Joseph B., George L. White Jr, and Harry Hatasaka. "*Timing intercourse to achieve pregnancy: current evidence.*" *Obstetrics & Gynecology* 100.6 (2002): 1333-1341, and Bigelow, Jamie L., et al. "*Mucus observations in the fertile window: a better predictor of conception than timing of intercourse.*" Human Reproduction 19.4 (2004): 889-892.

Just as the day of ovulation varies from cycle to cycle so does the timing of the six fertile days. The timing of the fertile window is highly variable, even among women who regard their menstrual cycles as regular. More than 70% of women are in their fertile window before day 10 or after day 17 of their menstrual cycle. The timing of the fertile window is even less predictable for women with less regular cycles.

The system according to the invention therefore provides particular advantages over all previously known systems that rely on counting the days of menstrual cycle and/or tracking fertility signs such as menstruation, basal body temperature and cervical fluid symptoms in terms of reliability and accuracy.

In an embodiment the obtained parameter is indicative of hyperventilation. Hyperventilation means that the rate and quantity of alveolar ventilation of carbon dioxide (CO2) exceeds the body's production of CO2.

For instance, it is accounted to hyperventilation that end-tidal carbon dioxide pressure (PetCO2) is significantly lower during the luteal phase than it is during the follicular phase. The PetCO2 exhibits a biphasic pattern during the menstrual cycle of women, wherein a decline of PetCO2 begins several days before ovulation. The decline of PetCO2 is a consequence of hyperventilation. Hyperventilation shows a significant drop in the days before ovulation which can be used for determining a beginning of the fertile window. It is an advantage of this embodiment of the present invention to determine a biomechanical parameter, which is easily and unobtrusively obtainable, and which is indicative of hyperventilation.

Each of these biomechanical parameters is indicative of respiration, can indicate hyperventilation and therefore advantageously be employed in determining the fertile window of the woman. Preferably, the contact sensor unit comprises a suitable sensor for measuring signals indicative of each of these parameters. Specific examples, which can of course also be provided in combination, will be explained in the context of further embodiments of the invention below.

In an embodiment the contact sensor unit is integrated into a bra. Since the bra is located on the thorax when worn by the woman, the contact sensor unit is already in a suitable position for determining biomechanical signals indicative of respiration. Further, since the system integrated into the bra is invisible to others when the woman wears the bra, nobody can see that the woman is wearing the system, and therefore the woman does not need to feel embarrassed. More specifically, since she does not show that she is trying to get pregnant and there is no indication to others that she or her partner is suffering from subfertility, the system allows for a more pleasant use.

In an embodiment the contact sensor unit is directly integrated into the bra. In other embodiments, the contact sensor unit is integrated in separable cups which can easily be removed in case the bra needs to get washed and the like. Preferably, the separable cups allow them to be put from one bra to another such that the system can advantageously be used with a plurality of bras.

Preferably, the contact sensor unit and the processing unit can both be integrated in the bra or the separable cups. Additionally or alternatively, the system comprises a transmitter unit for transmitting data to a separate device, such as including a phone, watch or laptop, which is configured to store and process the data.

In an embodiment the contact sensor unit is integrated in a wrist-worn device. The wrist-worn device includes, for instance, a wristband. In this embodiment, the wrist-worn device can include all units of the system, namely the contact sensor unit and at least the processing unit, while in other examples also at least part of the processing unit can be integrated distant from the wrist-worn device.

In an embodiment the system further comprises a communication unit for notifying of at least one of whether the woman is in her fertile window, when her fertile window will be, when her ovulation will take place, when her menstruation will take place.

The communication unit can, for instance, be implemented as a display of a smartphone or a wrist-worn device. In case the contact sensor unit is integrated in a bra, the communication unit is preferably distant from the contact sensor unit such that the woman can receive the information from the communication unit when wearing the bra. The indicated notifications are of course to be understood as examples, while other notifications are preferred in other embodiments.

In an embodiment the system further comprises a storing unit for storing at least one of the signal and the obtained parameter.

The storing unit preferably is located together with the processing unit and the contact sensor unit, such as all units being integrated in the bra. However, in other embodiments at least one of the processing unit, the contact sensor unit, the storing unit and the communication unit can also be located at a different position, such as being integrated in a separate device. In this embodiment, the system then includes a transmitter for transmitting data between the units. Data storage and processing is not limited to the bra-integrated system, the wrist-worn device and/or a smartphone, laptop computer and the like, but can additionally or alternatively also be implemented on a server, such as in the cloud.

The storing unit stores the signal and/or the obtained parameter preferably permanently or for a certain period of time. Preferentially, the storage signal and/or obtained parameter includes data from previous menstruation cycles, such that the data obtained from previous cycles can be taken as comparative values.

In an embodiment the system further comprises a user input unit for receiving user input on signs related to the menstrual cycle of the woman. Preferably the processing unit is configured to personalize the fertile window determination during a learning phase based on the user input.

Since the fertile window determination is personalized, the determination can be made more accurately. For instance, during the learning phase the woman can enter one or more of the known phases of her menstrual cycle, including the first day of the menstruation or the ovulation determined with another method, e.g. a urine stick, for one or more menstrual cycles.

In an embodiment the processing unit is configured to determine menstruation based on the fertile window, the parameter indicative of respiration or a change in the obtained parameter. Fertile periods are closely related to the menstrual cycle, the menstruation can therefore also be predicted in a similar way.

In an embodiment the system comprises at least one further sensor unit, preferably at least one further contact sensor unit, configured to obtain a physiological signal which is indicative of or influenced by the menstrual cycle. Preferably, a heart rate, a heart rate variability, a chloride ion concentration in sweat or a blood oxygenation (SpO2) can be provided by the further sensor unit. By taking variations in these parameters into account in addition to the signal provided by the contact sensor unit, the accuracy of the system can advantageously be improved. Additionally, the phase in the menstrual cycle can be given throughout the complete menstrual cycle, since the parameter is influenced by the menstrual cycle.

In an embodiment the system further comprises an activity determination unit for determining an activity of the woman. The processing unit is configured to relate the parameter indicative of respiration to the determined activity.

For instance, in case a respiration rate is employed as parameter indicative of respiration, a determined activity can be used for invalidating an increase of respiration rate, such that this increase is not accounted to, for instance, the fertility window. Expressed differently, since variations in the determined signal are accountable to the determined activity and not to fertility, the accuracy of the system can further be increased.

In an embodiment the system further comprises a transcutaneous CO2 sensor for non-invasively estimating a CO2 concentration of arterial blood of the woman, wherein the transcutaneous CO2 sensor preferably comprises at least one of a potentiometric sensor and an optical transcutaneous CO2 sensor.

Transcutaneous CO2 sensors are for instance available from SenTec and Radiometer and measure potentiometrically by determining the pH of an electrolyte layer. All sorts of CO2 sensors require the contact skin to be heated to an elevated temperature, such as between 40 and 42° C., such that the CO2 diffuses through the skin within an acceptable time. The optical transcutaneous CO2 sensor is preferred over the potentiometric sensor, since the potentiometric sensor comprises a membrane, which has to be replaced regularly, approximately once every two weeks, and requires regular recalibration. Exemplary optical transcutaneous CO2 sensors suitable for the present system are disclosed, for instance, in U.S. Pat. No. 9,316,594.

The CO2 concentration in the arterial blood can be used for assessing adequacy of ventilation, wherein the CO2 concentration decreases in case of hyperventilation. In particular, the CO2 concentration obtained using the transcutaneous CO2 sensor can beneficially be combined with the biomechanical parameter indicative of respiration to improve the accuracy of determination.

In an embodiment the processing unit is configured to determine a beginning of the fertile window of the woman based on a decrease of the estimated CO2 concentration or an increase of the minute volume, respiratory drive and respiration rate, respectively.

As indicated, a decrease of the estimated CO2 concentration indicates hyperventilation which comes along with the onset of the fertile window. Hyperventilation starts about seven days before ovulation and from that point the transcutaneous CO2 value will start to decrease. At the same time, biomechanical parameters such as minute volume, respiratory drive and respiration rate will all start to increase. This of course holds as long as the woman is at rest, expressed differently, as long as the woman is not carrying out a particular activity, including talking.

Preferably, in case the processing unit determines a decrease or increase of the respective biomechanical parameter, the system could validate the tendency the following day and, if the biomechanical parameters increase respectively decrease further, determine the beginning of the fertile window. Preferably, the woman can then be notified that her fertile window will start one day later.

In an embodiment the processing unit is configured to determine an end of the fertile window of the woman based on a determined plateau of the obtained biomechanical parameter after beginning of the fertile window. A plateau will be reached from about two days before ovulation until several days after ovulation. Preferably, having measured a constant value for about three consecutive days, representing the determination of a plateau, indicates that the end of the fertile window has been reached. Preferably, the user can be notified of the end of the fertile window, even more preferably the system could warn one day before that there is only one fertile day left.

In an embodiment the contact sensor unit comprises a bio-impedance sensor configured to be attached to the thorax of the woman, wherein the bio-impedance sensor is configured to obtain a signal indicative of a tidal volume.

In an embodiment the processing unit is configured to determine a minute volume based on a product of tidal volume and respiratory rate.

Preferably, the bio-impedance sensor of this embodiment is configured to derive the tidal volume, i.e. the lung volume of displaced air between normal inhalation and exhalation, from electrical impedances measured with contact with the user's skin. Preferably, the system further determines respiratory rate, such as by estimating a frequency of reoccurring measured impedances, and calculates the minute volume by multiplying tidal volume by respiratory rate. The respiratory rate preferably indicates the number of respiratory cycles per minute.

In an embodiment the contact sensor unit comprises an electromyography sensor configured to determine the electrical activity of muscles, preferably of intercostal parasternal muscles. The processing unit is configured to determine a respiratory drive from the determined electrical activity.

Respiratory drive can be described as a control and response of the respiratory system to control effort and rate of breathing, for instance. Electromyography (EMG) measures electrical activity of muscles, particularly the parasternal muscles responsible for breathing, and can thereby measure the effort to contract muscles, i.e. the effort to breathe in this application. Preferably, a surface EMG including three electrodes to be positioned on the intercostals parasternal muscles is used. If other circumstances do not change, hyperventilation would be indicated in case the respiratory drive increases. From a periodicity of the EMG signal, for instance, a respiration rate can also be measured.

In an embodiment the contact sensor unit comprises at least one of an inductance sensor and a stretch sensor for measuring an expansion of the thorax of the woman. In one embodiment, the contact sensor unit is integrated in a respiratory belt, while the inductance sensor and/or stretch sensor can be integrated in a chest band of a bra in other embodiments. The processing unit is configured to determine a respiration rate based on the measured expansion of the thorax.

In this embodiment, the expansion of the thorax is evaluated over time, wherein changes in the expansion pattern can be indicative of hyperventilation. Higher thorax expansion and/or higher respiration rate can be indicative of hyperventilation and used by this processing unit to determine onset and/or end of the fertile window. Inductance or stretch sensors are given as examples, in other embodiments the respiratory belt and/or bra can also include alternative or additional sensors for determining the expansion of the thorax.

In a further aspect a method for determining a fertile window of a woman is provided. The method comprises providing a signal in contact with the woman, wherein the signal is indicative of respiration of the woman, and processing the signal to obtain a biomechanical parameter indicative of respiration. The fertile window of the woman is determined based on a change in the obtained biomechanical parameter.

In a further aspect a computer program for determining a fertile window of a woman is provided, the computer program comprising program code means for causing a system as defined in claim 1 to carry out the method as defined in claim 14, when the computer program is run on the system.

It shall be understood that the system of claim 1, the method of claim 14 and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
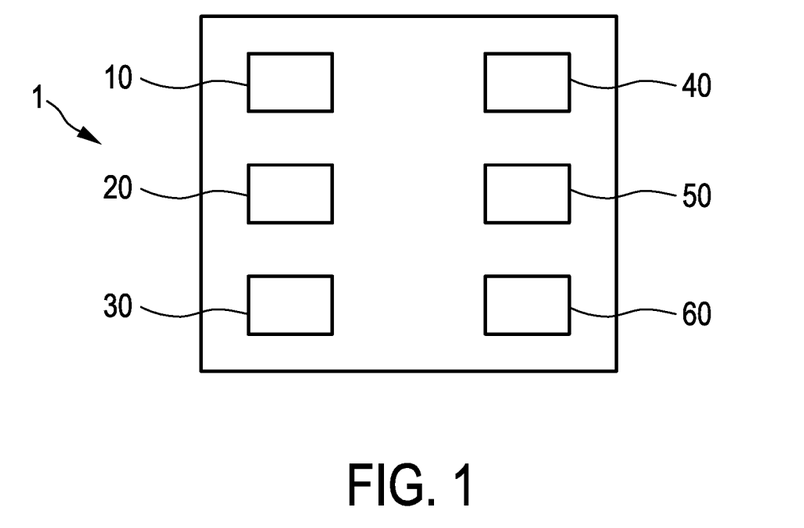
FIG. 1 shows schematically and exemplarily a system for determining a fertile window according to the invention.

FIG. 1 shows schematically and exemplarily a system 1 for determining a fertile window according to an embodiment of the invention. The system 1 comprises a contact sensor unit 10 for providing a signal in contact with the woman, wherein the signal is indicative of respiration of the woman, a processing unit 20 for processing the signal to obtain a biomechanical parameter indicative of respiration, a storage unit 30 and a feedback and communication unit 40. The system 1 tracks changes in ventilation and biomechanical signals of hyperventilation to estimate the woman's fertile window during her menstrual cycle.

Hyperventilation is one example of a parameter of respiration or ventilation that changes over the menstrual cycle. It can therefore be used as an indication for the fertile window. In this example, hyperventilation is detected by means of one or more contact sensors comprised in contact sensor unit 10. These sensors can measure, for instance, signals indicative of one or more of the following biomechanical parameters: tidal volume, respiration rate, respiratory drive, thorax expansion and/or minute ventilation. Particular examples of sensors for contact sensor unit 10 will be described with reference to some specific examples below.

Storage unit 30 is configured to store the data sensed by contact sensor unit 10 and/or data that are derived from the measured data. Expressed differently, storage unit 30 can store the data itself or parameters indicative of respiration derived from the sensed data. It is preferred that storage unit 30 stores data of a plurality of menstrual cycles so that processing unit 20 can analyze changes in the measured data and optionally compare these with changes in previous menstrual cycles.

Processing unit 20 is configured to analyze the changes in ventilation and preferably detect hyperventilation. From the detected hyperventilation and/or changes in ventilation, such as derived from biomechanical parameters derived from the sensed data, it determines the phase in the menstrual cycle and based thereon predicts when ovulation will take place.

Feedback unit 40 is configured to show the woman one or more of whether she is in her fertile window, when her fertile window will be, when her ovulation will take place, when her menstruation will take place and the like. Feedback unit 40 may be implemented by a smartphone or watch display, an LED indicator or another suitable notification means.

Optionally, system 1 further comprises at least one further sensor 50, in particular a further contact sensor, that measures physiological parameters that also vary with the menstrual cycle. For instance, further sensor 50 comprises at least one heart rate, heart rate variability, chloride ions, CO2 concentration or the like sensor. Data from further sensor 50 can be utilized by processing unit 20 to increase the reliability of the system.

Further optionally, system 1 comprises a user interface 60. User interface 60 is configured such that users can provide input to a system 1, preferably input on signs related to the menstrual cycle of the woman, for instance a time when her menstruation has started.

While all units of system 1 are depicted as within a common frame or casing in the example of FIG. 1, one, several or all of the units can be realized separate and distant from the remaining units. In this case, system 1 can provide suitable communication means such that the various units provided at different locations can communicate with each other. In one example, storage unit 30 and at least part of processing unit 20 can be implemented on a server, such that access to the data is provided on the server, for instance via an App or a web page. In other examples, storage unit 30 and/or processing unit 20 are implemented in the form of an App, which is downloadable via a well-known App store and executable on any type of smartphone, tablet, and the like. In another example, all of the components of system 1 are integrated in a bra or a wristband, such as a watch. These implementations can be combined and adapted to the particular requirements of an application, as obvious to a person skilled in the art.

The main embodiment of system 1 supports prediction of the fertile period or fertile window of a woman in a personal and unobtrusive way. The finding underlying the present invention is that hyperventilation, i.e. the rate and quantity of alveolar ventilation of carbon dioxide exceeds the body's production of carbon dioxide, varies with the menstrual cycle and shows a significant drop in the days before ovulation. The core concept of the present invention.

Figure 2:
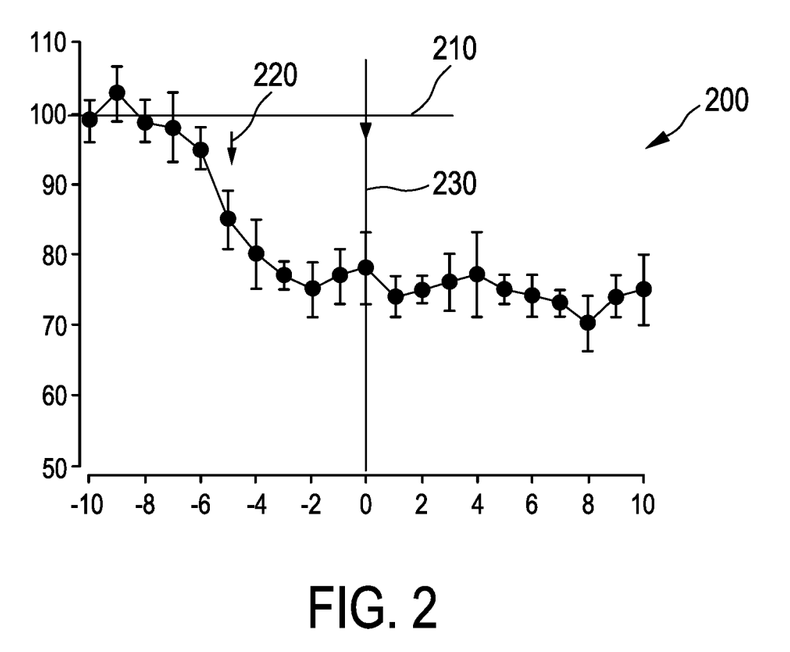
FIG. 2 shows schematically and exemplarily the course of expiratory CO2 during the menstrual cycle.

A biochemical origin of a measure indicative of hyperventilation is end-tidal carbon dioxide pressure (PetCO2), which is exemplarily illustrated in FIG. 2 over one menstrual cycle. Days from beginning of the luteinizing hormone (LH) peak are illustrated on the horizontal axis, end-tidal carbon dioxide pressure (PetCO2) normalized to the day of onset of the fertile window is illustrated on the vertical axis. The course of PetCO2 during the menstrual cycle is referred to as curve 200. A baseline 210 indicates a value at the beginning of the menstrual cycle, wherein at a day 220 PetCO2 is for the first time significantly lower than baseline 210. Between onset of fertile window 220 and ovulation 230 lies the fertile window. PetCO2 exhibits a biphasic pattern during the menstrual cycle, wherein the pattern is characterized by high baseline 210 values during the early and mid-follicular phase, a decline and a second plateau during the luteal phase. The decline of PetCO2 begins several days before ovulation 230, namely at the day indicated with 220. In FIG. 2, PetCO2 200 is drawn with error bars to both sides. Those error bars are exemplary for the experiment carried out with an exemplary number of 150 cycles which underlie the graph of FIG. 2. It can be seen that the decline of PetCO2 200 can be determined with high confidence.

Figure 3:
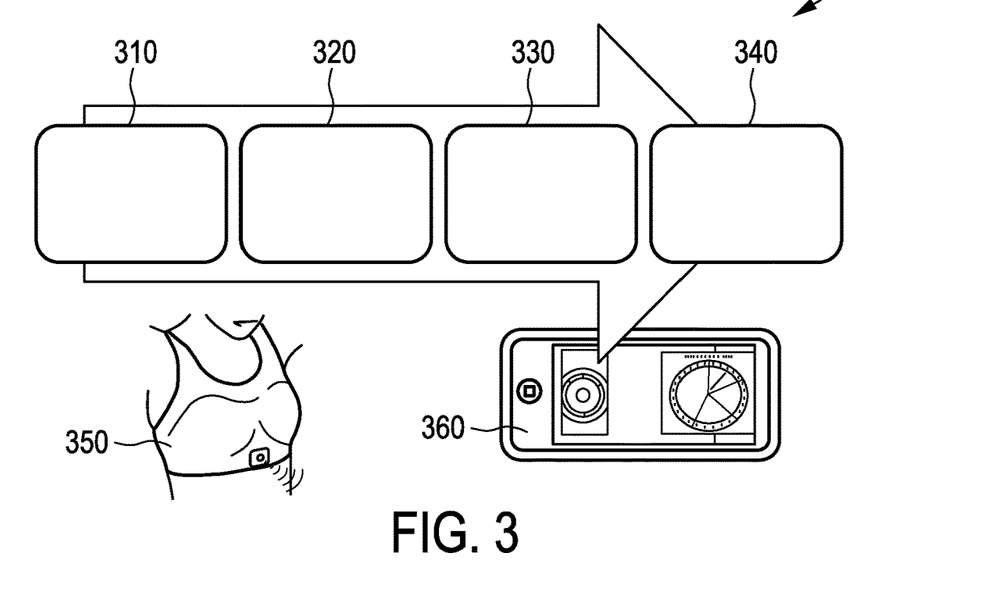
FIG. 3 shows schematically and exemplarily a process chain of using the system of FIG. 1.

FIG. 3 exemplarily summarizes a process chain 300 for the wearable system 1 for supporting personalized prediction of the fertile window. In a first step 310, contact measurements by contact sensor unit 10 show indications of changes in ventilation and hyperventilation. Based thereon, in step 320, data from contact sensor unit 10 is collected and, for instance, streamed to a mobile device, for instance a smartphone. In step 330, the streamed data is analyzed by algorithms, such as implemented in processing unit 20, which identify and categorize the menstrual cycle phase. In case an important information is determined in step 330, an alert may be generated and feedback may be provided in step 340. The relevant components in process chain 300 are a bra 350 and a smartphone running a dedicated App 360 which together form system 1 as disclosed with reference to FIG. 1. In this example, contact sensor unit 10 is provided in bra 350, wherein both processing unit 20 and storage unit 30 are integrated in smartphone 360. At the same time, smartphone 360 integrates feedback unit 40 and user interface 60. As mentioned before, different distributions of the various units among bra 350 and smartphone 360 are feasible.

Figure 4A:
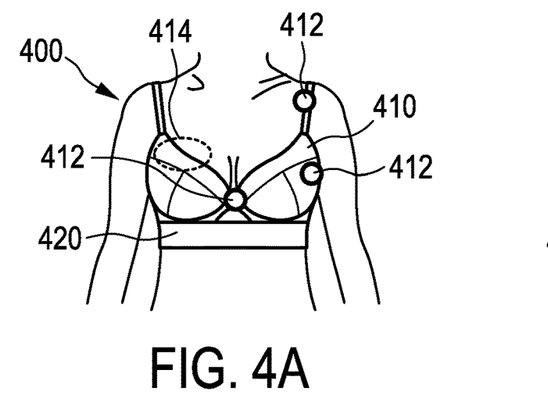
FIGS. 4A to 4C shows schematically and exemplarily three examples of implementing the system of FIG. 1.
Figure 4B:
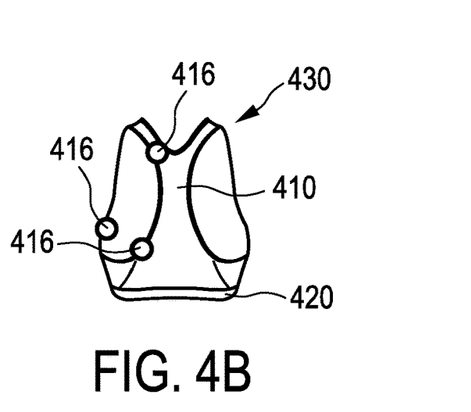
Figure 4C:
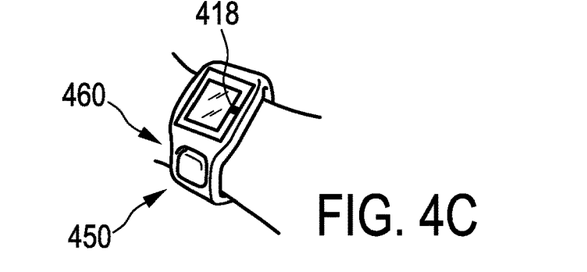

Specific sensor types and implementations are now described with further reference to FIGS. 4A to 4C. In the example of FIG. 4A, a sensor platform 400 comprising a bra 410 is illustrated which implements at least contact sensor unit 10 of system 1 as shown in FIG. 1. As discussed above, despite not being shown in FIG. 4A, sensor platform 400 can also include processing unit 20 and/or storage unit 30 and/or any of the further elements of system 1. In the example of FIG. 4A, sensor platform 400 comprises three tidal volume sensors 412 which are each directly integrated in bra 410. In an alternative example, sensors 412 are integrated in separable cups which then can be attached to any bra. Tidal volume sensors 412 can, for instance, comprise bio-impedance sensors which are located on the thorax, preferably at positions illustrated in more detail in FIG. 5. With this arrangement, it can be ensured that tidal volume sensors 412 be nicely placed on the thorax to ensure good measurements. Tidal volume sensors 412 can additionally be used to determine the minute ventilation from the measured tidal volume and a determined respiratory rate, while the respiratory rate can be deduced from a periodicity of the bio-impedance sensors. An increasing minute ventilation is, without an increase in activity, a sign for hyperventilation.

Independent from the form of particular sensor used, a bra is a preferred embodiment of the invention because it is invisible to others when dressed and therefore the woman does not need to feel embarrassed, i.e. as nobody can see that the woman is wearing the system, she does not show that she is trying to get pregnant and there is no indication to others that he or her partner is suffering from subfertility.

As indicated, alternatively sensors 412 could be integrated in cups that can be separated from the bra 410 or could be integrated in the bra that they can easily be removed in case the bra 410 needs to get washed. The cups and sensor arrangement could thus also be made such that they can easily be put from one bra 410 to another.

Instead of using electrodes as tidal volume sensors 412 to measure respiration rate from the bio-impedance signal, respiration rate and/or thorax expansion per breathing cycle itself can be measured in this example with a chest band 420 of the bra 410 comprising one or more stretch sensors, for instance. Hyperventilation would go along with a higher thorax expansion and/or a higher respiration rate.

While bio-impedance sensors are shown as examples of tidal volume sensors 412 in FIG. 4A, also other sensors such as electrodes for determining an electromyogram (EMG) of intercostals parasternal muscles can be employed. Based on the EMG on the parasternal muscles, respiratory effort could be determined. If other circumstances do not change, hyperventilation would take place if the respiratory drive increases. Besides respiratory drive, the sensors to determine EMG can also be used for determining respiratory rate.

Figure 5:
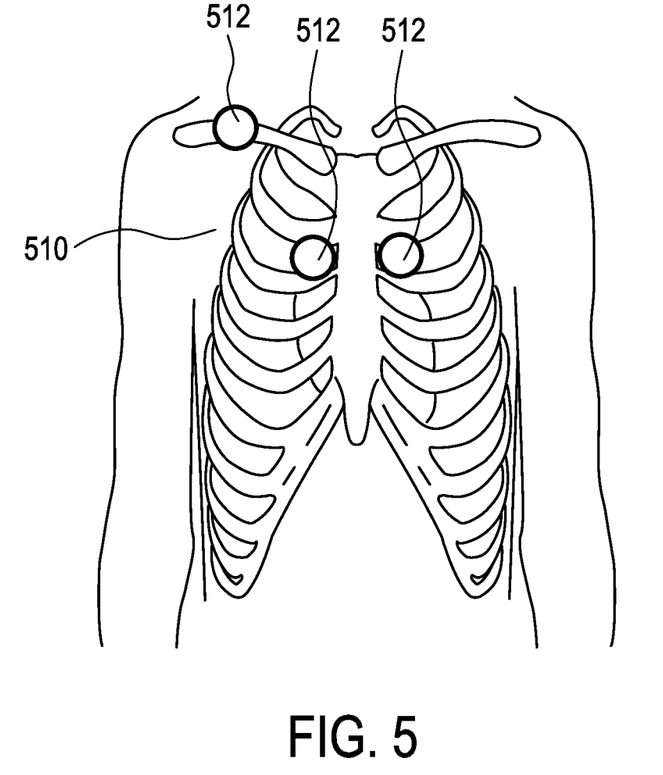
FIG. 5 shows schematically and exemplarily a positioning of electrodes on the chest.

FIG. 5 shows schematically and exemplarily the positioning of electrodes 512 on a chest 510 to measure bio-impedances or an EMG of intercostal parasternal muscles. While this arrangement of electrodes 512 is favorable, also other arrangements of electrodes 512 are of course contemplated.

Further, sensor platform 400 as shown in FIG. 4A comprises an additional sensor 414 in the form of a transcutaneous CO2 sensor. Transcutaneous CO2 sensor 414 uses locally heated electrochemical sensors which are applied to the skin surface and provide a non-invasive estimation of CO2 concentration in the arterial blood. For hyperventilation, the CO2 concentration determined by transcutaneous CO2 sensor 414 decreases. For instance, transcutaneous CO2 sensor 414 can measure potentiometrically by determining the pH of an electrolyte layer. Additionally or alternatively to potentiometrically determining the CO2 concentration, an optical transcutaneous CO2 sensor can be employed.

FIG. 4B shows a second sensor platform 430, in which tidal volume sensors 416 are integrated into a backside of bra 410. Also in this example, a chest band 420 can be provided to measure other physiological signals, such as heart rate, respiration rate, and/or chlorine concentration.

In the sensor platform 400 and/or the sensor platform 430, the at least one sensor 412, 414, 416 is integrated in the bra 410 for measuring at least one of respiration rate, tidal volume, minute volume, transcutaneous CO2 concentration and/or respiratory drive, and can therefore advantageously be placed on the thorax.

FIG. 4C shows a third sensor platform 450. In sensor platform 450, transcutaneous sensors 418 are integrated into a wristband 460, implemented in the form of a health watch. Transcutaneous CO2 sensor 418 is preferably placed at a volar side of the wrist instead of the upper side of the wrist because the skin is thinnest and therefore CO2 sensing works best, with the shortest time delay, on the volar side. Additionally or alternatively, other parameters related to a measurement of hyperventilation can be measured at the wrist, such as including a photoplethysmography (PPG), a chloride concentration and the like. Wristband 460 can contain the entire system 1, including contact sensor unit 10, processing unit 20, storage unit 30 and/or feedback unit 40 and user interface 60. However, wristband 460 can also be paired with a smartphone, tablet, and the like and one, more or all of the additional units can be integrated in the further device instead of wristband 460.

Likewise, storage unit 30, processing unit 20 and communication means can all be integrated in the bra 410. Alternatively, bra 410 contains a transmitter configured to transmit data to a separate device, such as a phone, watch, laptop and the like, which stores and processes the data and communicates the result to the user. Additionally or alternatively, data storage and processing can be done in the cloud instead of the separate device.

Returning to the preferred example of sensor platform 400 including transcutaneous CO2 sensor 412, the conditions of measurement are described in more detail in the following. Sensor platform 400, more precisely bra 410, does not need to be worn 24 hours a day seven days a week in order to complete the streaming. Instead, system 1 is in this example configured to monitor tidal volume CO2 concentrations day to day, while measurements are done once or twice per day. Transcutaneous sensor 414 warms up the skin to 40 to 42° C. until an equilibrium is reached in measured CO2 concentrations. The time the CO2 sensor 414 will be switched on is approximately 30 minutes. It is important that the CO2 value be captured during this period, i.e. while the sensor is being kept at this temperature, as soon as the woman has been at rest for at least 10 minutes. This is of importance, since activity can deteriorate the measurement result. The at least 10 minutes at rest, or at least not very active, can lie in the warm-up period, i.e. the period necessary to reach equilibrium. It is appreciated that the user has also not been talking for a prolonged period, since this could also deteriorate the captured measurement. To measure activity and/or talking an accelerometer or a microphone could be added to the system, for instance, or the system 1 could be coupled to an activity tracker or a sensor which is integrated in, for instance, a smartphone. After the measurement, transcutaneous sensor 414 and particularly its heater can be switched off such that skin burn can be prevented and power consumption can be limited. It is preferred that measurements be captured at the same moment on each day, for instance just after getting up. This also holds for alternative measurements of minute volume, tidal volume and/or respiration rate. It is preferred that measurements be obtained at about the same moment each day and not during or just after high activity or talking.

While transcutaneous sensor 414 relies on heating and needs a waiting period to reach equilibrium, time constraints are more relaxed with alternative parameters including minute volume, tidal volume, respiratory drive and/or respiration rate, which all can be measured instantaneously. For instance, these measurements could be taken as soon as the user has not talked or has not been active for about 3 to 5 minutes.

Figure 6:
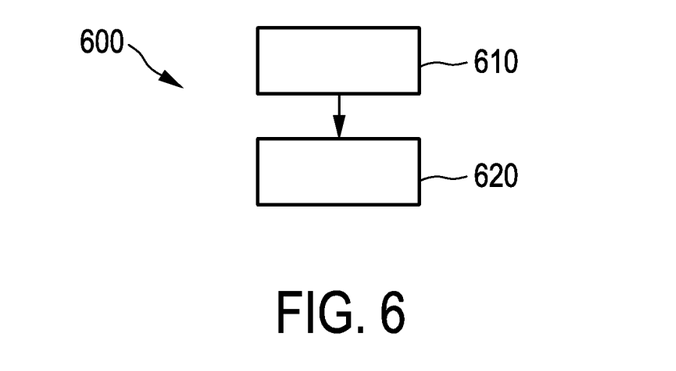
FIG. 6 shows schematically and exemplarily a flowchart of a method for determining a fertile window.

FIG. 6 shows schematically and exemplarily a flowchart of a method 600 for determining a fertile window. The method comprises a step 610 of providing a signal in contact with the woman, wherein the signal is indicative of respiration of the woman, and a step 620 of processing the signal to obtain a biomechanical parameter indicative of respiration, wherein the fertile window of the woman is determined based on a change in the obtained biomechanical parameter.

A computer program may be stored/distributed on a suitable medium, such as an optical storage medium or a solid-state medium, supplied together with or as part of other hardware, but may also be distributed in other forms, such as via the Internet or other wired or wireless telecommunication systems including being downloadable or purchasable via an app store.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

The invention claimed is:

1. A system for determining a fertile window of a woman, the system comprising:
   a contact sensor unit in contact with the woman, wherein the contact sensor unit includes a CO2 sensor and is configured to provide a signal indicative of respiration of the woman; and
   a processing unit configured to process the signal to obtain a biomechanical parameter indicative of the respiration, and determine the fertile window of the woman based on changes in the biomechanical parameter,
   wherein the biomechanical parameter includes at least one of a minute volume, a respiratory drive and thorax expansion.

2. The system according to claim 1, wherein the biomechanical parameter is indicative of hyperventilation.

3. The system according to claim 1, wherein the contact sensor unit is integrated in a wrist-worn device.

4. The system according to claim 1, further comprising a communication unit for notifying of at least one of whether the woman is in the fertile window, when the fertile window will be, and at least one of when ovulation will take place and when menstruation will take place.

5. The system according to claim 1, further comprising a storing unit for storing at least one of the signal and the biomechanical parameter.

6. The system according to claim 1, further comprising a user input unit for receiving user input on signs related to menstrual cycle of the woman, wherein the processing unit is configured to personalize determination of the fertile window during a learning phase based on the user input.

7. The system according to claim 1, further comprising an activity determination unit for determining an activity of the woman, wherein the processing unit is configured to relate the biomechanical parameter indicative of respiration to the determined activity.

8. The system according to claim 1, wherein the $CO_2$ sensor is configured to non-invasively estimate a $CO_2$ concentration of arterial blood of the woman, and wherein the $CO_2$ sensor comprises at least one of a potentiometric sensor and an optical $CO_2$ sensor.

9. The system according to claim 1, wherein the processing unit is configured to determine a beginning of the fertile window of the woman based on an increase of the minute volume, and the respiratory drive.

10. The system according to claim 1, wherein the contact sensor unit comprises at least one of:
a bio-impedance sensor configured to be attached to a thorax of the woman, wherein the bio-impedance sensor is configured to obtain a signal indicative of a tidal volume, wherein the processing unit is configured to determine the minute volume based on a product of the tidal volume and a respiratory rate,
an electromyography sensor configured to determine an electrical activity of intercostal parasternal muscles, wherein the processing unit is configured to determine the respiratory drive from the determined electrical activity, and
at least one of an inductance and a stretch sensor for measuring an expansion of the thorax of the woman, wherein the processing unit is configured to determine the respiration rate based on the measured expansion of the thorax.

11. The system according to claim 1, wherein the contact sensor unit is directly integrated into a bra to contact a skin of the woman.

12. The system according to claim 1, wherein the $CO_2$ sensor is configured to non-invasively estimate a $CO_2$ concentration of arterial blood of the woman, and wherein the processing unit is configured to determine a beginning of the fertile window of the woman based on an increase of the minute volume and the respiratory drive.

13. A method for determining a fertile window of a woman, the method comprising acts of:
providing a signal from contact sensor in contact with the woman, wherein the signal is indicative of respiration of the woman, and wherein the contact sensor includes a $CO_2$ sensor;
processing the signal to obtain a biomechanical parameter indicative of the respiration; and
determining the fertile window of the woman based on a change in the obtained biomechanical parameter,
wherein the biomechanical parameter includes at least one of a minute volume, a respiratory drive and thorax expansion.

14. A non-transitory computer readable medium comprising computer instructions which, when executed by a processor, configure the processor to cause performance the acts of the method of claim 13.

15. A system for determining a fertile window of a woman, the system comprising:
a $CO_2$ sensor configured to provide a signal indicative of a respiration of the woman; and
a processor configured to:
process the signal to obtain a biomechanical parameter indicative of the respiration, and
determine the fertile window of the woman based on a change in the obtained biomechanical parameter,
wherein the biomechanical parameter includes at least one of a minute volume, a respiratory drive and thorax expansion.

16. The system according to claim 15, wherein the sensor is a contact sensor configured to contacts a skin of the woman.

* * * * *